(12) United States Patent
Kim et al.

(10) Patent No.: US 12,121,024 B2
(45) Date of Patent: Oct. 22, 2024

(54) METHOD FOR VITRIFICATION AND THAWING OF OOCYTE OF CANINE AND FROZEN-THAWED OOCYTE PRODUCED USING THE SAME

(71) Applicants: MKBIOTECH. CO. LTD, Daejeon (KR); THE INDUSTRY & ACADEMIC COOPERATION IN CHUNGNAM NATIONAL UNIVERSITY (IAC), Daejeon (KR)

(72) Inventors: Min Kyu Kim, Daejeon (KR); Yoon Seok Nam, Nonsan-si (KR); Kang sun Park, Sejong-si (KR); Gook Bin Ji, Incheon (KR); Ji Hye Lee, Deajeon (KR)

(73) Assignees: MKBIOTECH. CO. LTD, Daejeon (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 266 days.

(21) Appl. No.: 16/616,488

(22) PCT Filed: Jul. 18, 2019

(86) PCT No.: PCT/KR2019/008861
§ 371 (c)(1),
(2) Date: Nov. 24, 2019

(87) PCT Pub. No.: WO2020/213789
PCT Pub. Date: Oct. 22, 2020

(65) Prior Publication Data
US 2021/0352888 A1   Nov. 18, 2021

(30) Foreign Application Priority Data
Apr. 19, 2019   (KR) .................. 10-2019-0045801

(51) Int. Cl.
*C12N 5/075*   (2010.01)
*A01N 1/02*   (2006.01)

(52) U.S. Cl.
CPC ......... *A01N 1/0284* (2013.01); *C12N 5/0609* (2013.01)

(58) Field of Classification Search
None
See application file for complete search history.

(56) References Cited

FOREIGN PATENT DOCUMENTS

| JP | 2000189155 A | 7/2000 |
|----|--------------|--------|
| JP | 2000197481 A | 7/2000 |
| JP | 2001226201 A | 8/2001 |
| JP | 2007126471 A | 5/2007 |
| JP | 2009005584 A | 1/2009 |
| KR | 20150029191 A | 3/2015 |

OTHER PUBLICATIONS

Tharasanit (2021, Animals, 11:2949, 17 pages).*
Songsasen (Anim Reprod Sci. Mar. 2007 ; 98(1-2): 2-22).*
Tanslation of Park, Korean J. Emb. Trans., 17:2, 117-121.*
International Search Report of PCT/KR2019/008861, English translation, Jan. 17, 2020.
S. H. Park et al, Studies on In Vitro Fertilization after Vitrification Freezing of Immatured Canine Oocytes, the Korean Society of Embryo Transfer. 2002, vol. 17, No. 2, pp. 117-121, Namwon, South Korea.
Office Action from China Intellectual Property office of 2019800024219, Jul. 23, 2021.
S. Boutelle et al, Vitrification of oocytes from endangered Mexican gray wolves (*Canis lupus baileyi*), Science Direct Theriogenology, 2011, vol. 75,pp. 647-654, Elsevier, Amsterdam, Netherlands.
Office Action from Japan Patent Office of 2019-565553, Oct. 5, 2021.
I. Willmut, A. E. Schnieke et al, Viable offspring derived from fetal and adult mammalian cells, letters to nature, Feb. 27, 1997, vol. 385, pp. 810-813, 1997 Nature Publishing Group, Berlin, Germany.
Jose B. Cobelli et al, Cloned Transgenic Calves Produced from Nonquiescent Fetal Fibroblasts, Science, May 22, 1998, vol. 280, pp. 1256-1258, American Association for the Advancement of Science, Washington DC, USA.
Yoko Kato et al, Eight Calves Cloned from Somatic Cells of a Single Adult, Science, Dec. 11, 1998, vol. 282, pp. 2095-2098, American Association for the Advancement of Science, Washington DC, USA.
T. Wakayama et al, Full-term development of mice from enucleated oocytes injected with cumulus cell nuclei, Nature, Jul. 23, 1998, vol. 394, pp. 369-374, Macmillan Publishers, New York, USA.
Alexander Baguisi et al, Production of goats by somatic cell nuclear transfer, Nature Biotechnology, May 17, 1999, vol. 17, pp. 456-461, Nature America, Inc. New York, USA.
Irina A. Polejaeva et al, Cloned pigs produced by nuclear transfer from adult somatic cells, letters to nature, Sep. 7, 2000, vol. 407, pp. 86-90, Macmillan Magazines Ltd, New York, USA.

(Continued)

*Primary Examiner* — Valarie E Bertoglio
(74) *Attorney, Agent, or Firm* — STIP Law Group, LLC

(57) ABSTRACT

The present invention relates to a method for vitrification and thawing of oocytes of animals for somatic cell cloning. More specifically, the present disclosure relates to a method for vitrification and thawing of canine oocytes, and to thus produced frozen-thawed oocytes. In a conventional approach of the vitrification-frozen oocyte production for the dog, an estrous cycle may not coincide with an experimental schedule. However, the method for vitrification and thawing of the canine oocyte according to the present disclosure and the resulting frozen-thawed oocyte allows an experimental schedule to coincide with the estrous cycle, resulting in high nuclear transfer and fertilization effects.

2 Claims, 4 Drawing Sheets

(56) References Cited

OTHER PUBLICATIONS

G.S. Im et al, Effect of Protein Supplementation, O2 Concentration and Co-Culture on the Development of Embryos Produced by Nuclear Transfer Using Cultured Cumulus Cells in Hanwoo (Korean Cattle), National Livestock Research Institute, RDA, Apr. 27, 2001, pp. 1260-1265, National Livestock Research Institute, Wanju, Republic of Korea.

Y, Heyman et al, Novel Approaches and Hurdles to Somatic Cloning in Cattle, Cloning and Stem Cells, 2002, vol. 4, pp. 47-55, Mary Ann Liebert, Inc. New York, USA.

Taeyoung Shin et al, A cat cloned by nuclear transplantation, Nature, Feb. 21, 2002, vol. 415, p. 859, Macmillan Magazines Ltd, New York, USA.

Xiao-Yu Yang et al, Effect of individual heifer oocyte donors on cloned embryo development in vitro, Animal Reproduction Science, Feb. 1, 2007, vol. 104, pp. 28-37, Elsevier, Amsterdam, Netherlands.

Eun Young Kim et al, In Vitro Development of Somatic Cell Nuclear Transfer Embryo Treated with Flavonoid and Production of Cloned Jeju Black Cattle, Reprod Dev Biol, 2010, vol. 34, pp. 127-134, Ministry of Agriculture, Food and Rural Affairs, Sejong-si, Republic of Korea, English translation of abstract.

Mohammad Shamim Hossein et al, Influence of season and parity on the recovery of in vivo canine oocytes by flushing fallopian tubes, Animal Reproduction Science, 2007, vol. 99, pp. 330-341, Elsevier, Amsterdam, Netherlands.

Mohamed Fathi et al, Improvement of the developmental competence of canine oocyte using caffeine supplementation during IVM at different maturation time, Zygote, 2018, pp. 1-6, Cambridge University of Press, Cambridge, United Kingdom.

Byeong Chun Lee et al, Dogs cloned from adult somatic cells, Brief Communications, Aug. 4, 2005, vol. 436, pp. 641-649, Nature, Berlin, Germany.

* cited by examiner

METHOD FOR VITRIFICATION AND THAWING OF OOCYTE OF CANINE AND FROZEN-THAWED OOCYTE PRODUCED USING THE SAME

CROSS-REFERENCE TO RELATED APPLICATIONS

This application is the U.S. National Phase under 35 U.S.C. § 371 of International Application No. PCT/KR2019/008861 filed on Jul. 18. 2019, which in turn claims the benefit of Korean Application No. 10 2019 0045801, filed on Apr. 19, 2019, the disclosures of which are incorporated by reference into the present application.

TECHNICAL FIELD

The present disclosure relates to a method for vitrification and thawing of oocytes of animals for somatic cell cloning. More specifically, the present disclosure relates to a method for vitrification and thawing of canine oocytes, and to thus produced frozen-thawed oocytes.

BACKGROUND ART

Somatic cell cloning includes removing a nucleus from an oocyte and transplanting a nucleus of a somatic cell to be cloned thereto to create a clone with the same genetic information as the somatic cell. The somatic cell cloning becomes a breakthrough approach that allows creation of life via somatic cell nuclear transfer without oocyte and sperm coupling. Currently, the somatic cell cloning has been used in a variety of practical applications, such as production of useful animals, production of transformed animals for production of expensive drugs, cloning of endangered animal species, cloning of pets, and regenerative medicine.

The somatic cell cloning involves an enucleation process in which a nucleus is removed from a donor egg, a nuclear transfer process of transplanting a somatic cell into the denucleated donor egg, a cell fusion process between the somatic cell and the donor egg, an ovum activation process to induce cytoplasmic activity of the cell-fused donor egg, and a culture process of the somatic cell cloned embryo. Those processes require sophisticated mechanical techniques and chemical treatments using long-term micromanipulators in vitro. The cloning requires a donor egg and a somatic cell with genetic information to be replicated as a base material. A clone animal using a somatic cell as first reported was a sheep by Wilmut et al. in England in 1997. Then, a clone animal using a somatic cell was a mouse (Wakayama et al., 1998), a goat (Baguisi et al., 1999), a swine (Polejaeva et al., 2000), a rabbit (Chesne et al., 2002), a cat (Shin et al., 2002). That is, the cloning has been reported in a variety of species. Research results of a cloned cow were reported by Kato and Cibelli et al. in 1998. In Korea, Im et al. (2001) and Kim et al. (2010) reported production of a cloned cow. However, efficiency of the somatic cell based clone production is known to be smaller than 5% (Heyman et al., 2002; Yang et al. 2008).

For the somatic cell cloning, the somatic cell may be frozen and then thawed for use when necessary at any time. Many somatic cells may be obtained through a proliferation process. Thus, even when some thereof are lost, the somatic cell cloning may be performed using the remaining cells. That is, the somatic cell freezing method is already common and has a high cell survival ratio, thereby making it difficult to secure cells to be used for cloning a somatic cell.

On the other hand, the donor egg may only be collected from an ovary that is obtained during slaughter of an animal. Thus, when sudden natural disasters, such as foot and mouth disease, the slaughter of the animal may be difficult. Thus, the ovaries may not be supplied and thus fresh eggs may be supplied and thus the somatic cell cloning may not be realized. Thus, it is necessary to cryopreserve unfertilized oocytes for continued supply of oocytes. In addition, efforts are being made worldwide to protect and revive endangered or reproductivity-deteriorated animals due to environmental pollution or natural destruction. When a good quality oocyte is selected and stored in advance, the oocyte may be usefully used not only for the somatic cell cloning studies but also for other studies requiring the oocyte.

A key issue for cryopreservation involves treatment of water, which accounts for about 90% of a cell. The water forms sharp ice crystals during a freezing process, which causes a cell membrane to be damaged, causing the cells to die after thawing the cells. A mammalian oocyte is about 50,000 times larger in size compared with a size of a normal somatic cell or sperm and is about 120 to 150 μm in size. The mammalian oocyte has more water than other cells have. The cryopreservation of a mature oocyte thereof may be difficult because chromosomes and chromosome cleavage mechanisms that separate the chromosomes are directly exposed in a cytoplasm. Therefore, an scheme to safely protect the oocyte after the freezing process is required. Additionally, a technique for increasing a viability of the oocyte even after freezing and thawing the oocyte is required.

In particular, unlike other mammals, canines have a unique breeding physiological system in which an immature oocyte ovulates and matures after 2 to 3 days in a uterine tube and then fertilized. A timing of the oocyte collection from the body leads to an outcome. As a result, to deal with a case when an experimental canine having the same estrus timing is not obtained, there is a need for a technique to secure a sufficient amount of oocytes via vitrification. This technique and result thereof are currently poor.

DISCLOSURE

Technical Problem

Unlike other mammals, canines have a unique breeding physiological system in which an immature oocyte ovulates and matures after 2 to 3 days in a uterine tube and then fertilized. A timing of the oocyte collection from the body leads to an outcome. As a result, to deal with a case when an experimental canine having the same estrus timing is not obtained, there is a need for a technique to secure a sufficient amount of oocytes via vitrification. This technique and a result thereof is currently poor.

In addition, attempts have been made to freeze immature oocytes in the dog.

However, an in vitro maturation system is still insufficient and thus may not be used in vitrification of a mature oocyte. Thus, utilization of a somatic cell replication in the dog is insufficient.

Thus, the present disclosure is to provide a method for collecting a mature oocyte of the canine and for preforming vitrification of the oocyte, and to provide a frozen oocyte produced according to this method.

Technical Solution

The present disclosure is intended to address the purpose and requirement. Thus, the present disclosure provides a method for vitrification and thawing of an oocyte of a canine. The method includes:
- a process of collecting a mature oocyte from a canine (process 1);
- a process of performing a vitrification process of the collected oocyte (process 2),
  wherein the process of performing the vitrification process of the collected oocyte includes:
    preparing a mixed liquid, an equilibrium solution, an vitrification solution (process 2-1);
  wherein the mixed liquid includes a mixture between 300 to 1000 parts by weight of modified HTF medium-HEPES with gentamicin (mHTF) and 100 parts by weight of 10 to 30% serum substitute supplement (SSS),
    wherein the equilibrium solution contains 6.5 to 8.5% (v/v) ethylene glycol, 6.5 to 8.5% (v/v) dimethyl sulfoxide, 10 to 30% dextran serum supplement, and HEPES butter solution containing 25 to 45 μg/ml of gentamicin sulfate,
    wherein the vitrification solution contains 5 to 25% (v/v) ethylene glycol, 5 to 25% (v/v) dimethyl sulfoxide, 10 to 30% dextran serum supplement, 0.3 to 0.6 M of sucrose, and HEPES butter solution containing 25 to 45 μg/ml gentamicin sulfate,
    a denuding process of removing a cumulus cell of the collected oocyte (process 2-2);
    a process of treating the mature oocyte from which the cumulus cell is removed using the mixed liquid equilibrated to a room temperature state (process 2-3);
    a process of adding the equilibrium solution to the mixed liquid containing the oocyte and treating the oocyte using the mixed solution and then adding the equilibrium solution again to the mixed liquid containing the oocyte and again treating the oocyte using the mixed solution (process 2-4);
    a process of treating the treated oocyte with the equilibrium solution (process 2-5);
    a process of transferring the treated oocyte to the vitrification solution and treating the oocyte with the vitrification solution (process 2-6); and
    a process of placing the oocyte on an oocyte freezing tool and removing the vitrification solution therefrom and then immediately storing the oocyte in liquid nitrogen (process 2-7).
- Further, the method further includes a process of thawing the vitrification-frozen oocyte (process 3),
  wherein the process of thawing the vitrification-frozen oocyte (process 3) includes:
    a process of preparing a thawing solution, a dilution solution, a washing solution, and a recovery medium (process 3-1),
    wherein the thawing solution contains 0.5 to 1.5 M of sucrose, 10 to 30% dextran serum supplement, and HEPES butter solution containing 25 to 45 μg/ml of gentamicin sulfate,
    wherein the dilution solution contains 0.3 to 0.7 M of Sucrose, 10 to 30% dextran serum supplement, and HEPES butter solution containing 25 to 45 μg/ml of gentamicin sulfate,
    wherein the recovery medium includes a mixture of HEPES butter solution, sodium pyruvate, gentamicin sulfate, FBS (Fetal Bovine Serum),
    a process of heating the thawing solution to 35 to 40° C. in an incubator (process 3-2);
    a process of heating the recovery medium to 35 to 40° C. in the incubator (process 3-3);
    a process of withdrawing the oocyte freezing tool (CryoTop) stored in the liquid nitrogen and heating the tool and inputting the tool into the thawing solution and then separating the oocyte attached to the oocyte freezing tool (CryoTop) and treating the separated oocyte (process 3-4);
    a process of transferring the separated oocyte to the dilution solution equilibrated to a room temperature state and treating the oocyte with the dilution solution (process 3-5);
    a process of sequentially transferring and treating the treated oocyte to two of the washing solutions equilibrated to a room temperature state (process 3-6); and
    a process of transferring the oocyte to the heated recovery medium for recovery culture and then culturing the oocyte in the recovery medium (process 3-7).

Further, the present disclosure provides a frozen-thawed oocyte produced by the method for vitrification and thawing of the oocytes of the canine.

Advantageous Effects

The vitrification method of the canine oocyte according to the present disclosure may use the mixed liquid, equilibrium solution, and vitrification solution. Thus, due to the technical characteristics of the vitrification and the mixed liquid, equilibrium solution, and vitrification solution, ice crystal formation in the oocyte is prevented and much of the water in the cell is removed during the freezing process. Further, in the vitrification method of the canine oocyte, the oocyte is immediately input to the liquid nitrogen and frozen therein, thereby achieving an ultra-fast freezing method. Thus, the ice crystal formation may be prevented such that the cell wall and membrane are protected, and toxicity is markedly reduced, and thus the cell viability is markedly increased.

Further, the method of thawing the canine oocyte according to the present disclosure may use the thawing solution, dilution solution, washing solution, recovery medium and the above thawing process. Thus, due to the technical characteristics of the thawing solution, dilution solution, washing solution, and recovery medium and thawing process, the viability of the frozen-thawed oocyte is markedly increased, and thus, the frozen-thawed oocyte resulting from the method in accordance with the present disclosure has high nuclear transfer culture effect.

Further, in the conventional approach of the vitrification-frozen oocyte production for the dog, an estrous cycle may not coincide with an experimental schedule. However, the method for vitrification and thawing of the canine oocyte according to the present disclosure and the resulting frozen-thawed oocyte allows an experimental schedule to coincide with the estrous cycle, resulting in high nuclear transfer and fertilization effects.

BEST MODE

Figure 1:
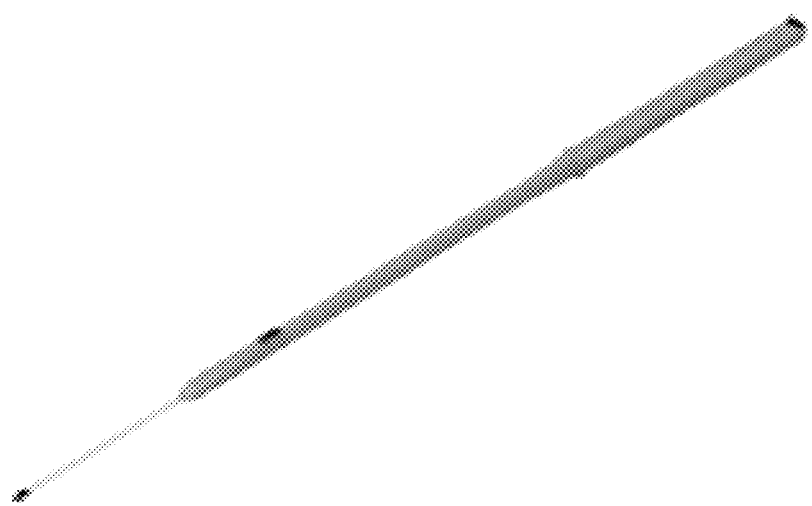
FIG. 1 shows CryoTop (Kitazato, Japan) as an oocyte freezing tool according to an embodiment of the present disclosure.

The present disclosure is directed to a method for vitrification and thawing of an oocyte of a canine. The method includes: a process of collecting a mature oocyte from a canine (process 1); a process of performing a vitrification process of the collected oocyte (process 2), wherein the process of performing the vitrification process of the collected oocyte includes: preparing a mixed liquid, an equilibrium solution, an vitrification solution (process 2-1); a denuding process of removing a cumulus cell of the collected oocyte (process 2-2); a process of treating the mature oocyte from which the cumulus cell is removed using the mixed liquid equilibrated to a room temperature state (process 2-3); a process of adding the equilibrium solution to the mixed liquid containing the oocyte and treating the oocyte using the mixed solution and then adding the equilibrium solution again to the mixed liquid containing the oocyte and again treating the oocyte using the mixed solution (process 2-4); a process of treating the treated oocyte with the equilibrium solution (process 2-5); a process of transferring the treated oocyte to the vitrification solution and treating the oocyte with the vitrification solution (process 2-6); and a process of placing the oocyte on an oocyte freezing tool and removing the vitrification solution therefrom and then immediately storing the oocyte in liquid nitrogen (process 2-7).

[Modes]

Hereinafter, the present disclosure will be described in detail with reference to the accompanying drawings.

The present disclosure provides a canine vitrification-frozen oocyte production method and a canine frozen oocyte produced according to the vitrification-frozen oocyte production method.

In accordance with the present disclosure, the method first collects a mature oocyte of the canine (process 1).

In the present disclosure, the canine includes fox, raccoon dog, wolf, wild dog, and domestic dog.

The method in accordance with the present disclosure involves collection of mature oocytes surgically from a 1 to 5-year-old estrus dog.

In particular, in the method of the present disclosure, blood is taken daily from the dog since a date when estrus is observed and then progesterone (P4) in serum was measured using Vetchroma (Anivet, Korea). A day when the progesterone concentration is greater than 10 ng/ml was defined as an ovulation day. At 72 hours after the day, the matured nucleated oocytes are collected from the dog body through surgical surgery.

The process of collecting the nucleated oocytes is performed while anesthetizing the estrus dog with 5 to 7 mg/ml, preferably 6 mg/ml ketamine, and maintaining the anesthesia with 1.5 to 2.5%, preferably 2% isoflurane.

After opening the stomach and removing the uterus and fixing the same, a flushing needle is attached to a start point of an oviduct through a slit of versa surrounding the ovary. Then, an IV catheter is inserted into the oviduct adjacent to a oviduct junction. Then, the matured oocyte is collected using a flushing medium.

The method in accordance with the present disclosure performs the vitrification process of the oocytes as collected above (process 2).

The vitrification process of the collected oocyte in accordance with the present disclosure is carried out in following steps.

The technical characteristics of the method the present disclosure are related to compositions of the mixed liquid, equilibrium solution and vitrification solution used in the vitrification process below.

The vitrification method of the canine oocyte according to the present disclosure may use the mixed liquid, equilibrium solution, and vitrification solution. Thus, due to the technical characteristics of the vitrification and the mixed liquid, equilibrium solution, and vitrification solution, ice crystal formation in the oocyte is prevented and much of the water in the cell is removed during the freezing process. Further, in the vitrification method of the canine oocyte, the oocyte is immediately input to the liquid nitrogen and frozen therein, thereby achieving an ultra-fast freezing method. Thus, the ice crystal formation may be prevented such that the cell wall and membrane are protected, and toxicity is markedly reduced, and thus the cell viability is markedly increased.

The process of performing the vitrification process of the collected oocyte (process 2) may include preparing a mixed liquid, an equilibrium solution, an vitrification solution (process 2-1).

In one embodiment, the mixed liquid includes a mixture between modified HTF medium-HEPES with gentamicin (mHTF) and serum substitute supplement (SSS).

In one embodiment, the mixed liquid includes a mixture between 300 to 1000 parts by weight of modified HTF medium-HEPES with gentamicin (mHTF) and 100 parts by weight of 10 to 30% serum substitute supplement (SSS).

In one embodiment, the mixed liquid includes a mixture between modified HTF medium-HEPES with gentamicin (mHTF) and 20% serum substitute supplement (SSS).

In one embodiment, the equilibrium solution contains ethylene glycol, dimethyl sulfoxide, dextran serum supplement, and HEPES butter solution containing gentamicin sulfate.

In one embodiment, the equilibrium solution contains 6.5 to 8.5% (v/v) ethylene glycol, 6.5 to 8.5% (v/v) dimethyl sulfoxide, 10 to 30% dextran serum supplement, and HEPES butter solution containing 25 to 45 μg/ml of gentamicin sulfate. The equilibrium solution is equilibrated to a room temperature state.

In the present disclosure, the HEPES butter solution containing the gentamicin sulfate may be used under a name TCM199 (trade name).

In one embodiment, the equilibrium solution contains 7.5% (v/v) ethylene glycol, 7.5% (v/v) dimethyl sulfoxide, 20% dextran serum supplement, and HEPES butter solution (TCM199: trade name) containing 35 μg/ml of gentamicin sulfate. The equilibrium solution is equilibrated to a room temperature state.

In one embodiment, the vitrification solution contains ethylene glycol, dimethyl sulfoxide, dextran serum supplement, sucrose, and HEPES butter solution containing gentamicin sulfate. The vitrification solution is equilibrated to a room temperature state.

In one embodiment, the vitrification solution contains 5 to 25% (v/v) ethylene glycol, 5 to 25% (v/v) dimethyl sulfoxide, 10 to 30% dextran serum supplement, 0.3 to 0.6 M of sucrose, and HEPES butter solution containing 25 to 45 µg/ml gentamicin sulfate. The vitrification solution is equilibrated to a room temperature state for 0.5 to 2 hours.

In one embodiment, the vitrification solution contains 15% (v/v) ethylene glycol, 15% (v/v) dimethyl sulfoxide, 20% dextran serum supplement, 0.5 M of sucrose, and HEPES butter solution containing 35 µg/ml gentamicin sulfate. The vitrification solution is equilibrated to a room temperature state for 0.5 to 2 hours.

As used herein, the term "equilibrating" means allowing a concentration of a mixed solution is uniform and keeping the solution to have a state similar to the room temperature state to be used at room temperature.

The method in accordance with the present disclosure includes a denuding process of removing a cumulus cell of the collected oocyte (process 2-2). In this process, hyaluronidase may be used.

In one embodiment, the method in accordance with the present disclosure includes a denuding process of removing a cumulus cell of the collected oocyte using 0.01 to 0.2% hyaluronidase.

In one embodiment, the method in accordance with the present disclosure includes a denuding process of removing a cumulus cell of the collected oocyte using 0.1% hyaluronidase. Then, the method in accordance with the present disclosure includes examine whether the oocyte is mature.

The method in accordance with the present disclosure includes a process of treating the mature oocyte from which the cumulus cell is removed using a drop of 10 to 30 µl of the mixed liquid equilibrated to a room temperature state for 0.5 to 2 minutes (process 2-3).

As used in the present disclosure, the drop refers to a drop in a form of droplet.

In one embodiment, the method in accordance with the present disclosure includes a process of treating the mature oocyte from which the cumulus cell is removed using a drop of 20 µl of the mixed liquid (mHTF solution containing 20% SSS) equilibrated to a room temperature state for 1 minute.

The method in accordance with the present disclosure includes a process of adding a drop of 10 to 30 µl of the equilibrium solution to the mixed liquid containing the oocyte and treating the oocyte using the mixed solution for 1 to 3 minutes and then adding a drop of 10 to 30 µl of the equilibrium solution again to the mixed liquid containing the oocyte and again treating the oocyte using the mixed solution for 1 to 3 minutes (process 2-4).

In one embodiment, the method in accordance with the present disclosure includes a process of adding a drop of 20 µl of the equilibrium solution to the mixed liquid containing the oocyte and treating the oocyte using the mixed solution for 2 minutes and then adding a drop of 20 µl of the equilibrium solution again to the mixed liquid containing the oocyte and again treating the oocyte using the mixed solution for 2 minutes.

The method in accordance with the present disclosure includes a process of treating the treated oocyte with the equilibrium solution for 5 to 7 minutes (process 2-5).

In one embodiment, the method in accordance with the present disclosure includes a process of treating the treated oocyte with a drop of 20 µl of the equilibrium solution for 6 minutes.

Figure 2:
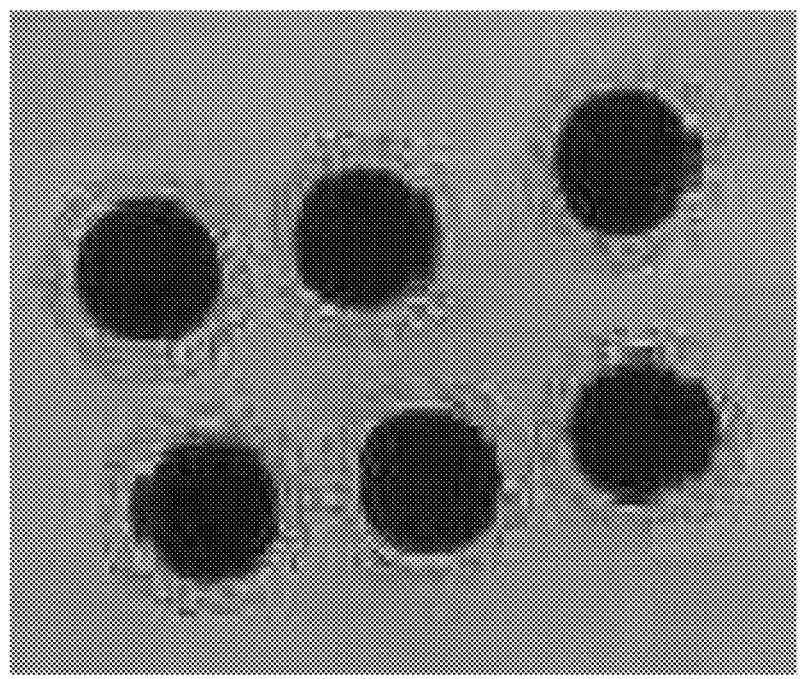
FIG. 2 is a photograph of a state of a mature oocyte in a process of vitrification and thawing of the mature oocyte in a dog.
Figure 3:
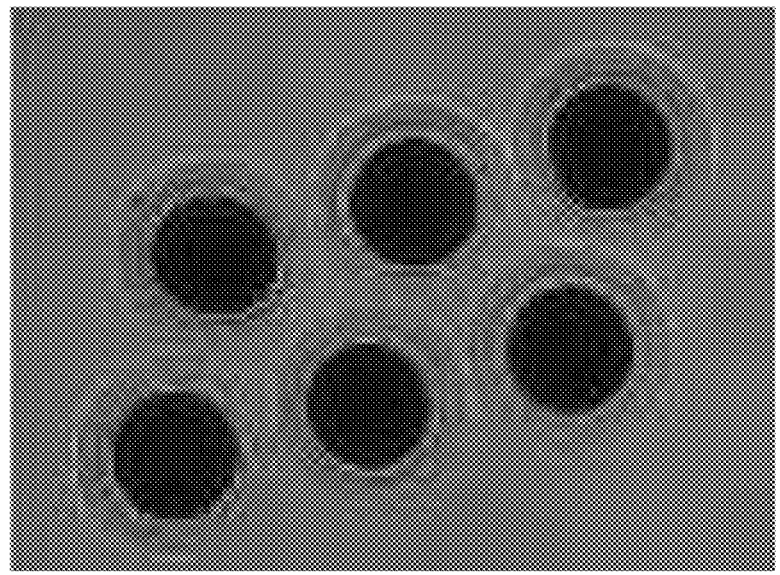
FIG. 3 is a photograph of a state of a mature oocyte in a process of vitrification and thawing of the mature oocyte in a dog.

FIG. 2 is a photograph before vitrification of the oocyte. FIG. 3 shows a photograph of the oocyte treated with the equilibrium solution.

The method in accordance with the present disclosure includes a process of transferring the treated oocyte to the vitrification solution and treating the oocyte with the vitrification solution for 0.5 to 3 minutes (process 2-6).

In one embodiment, the method in accordance with the present disclosure includes a process of transferring the treated oocyte to a drop of 50 µl of the vitrification solution and treating the oocyte with the vitrification solution for 1 minute.

Figure 4:
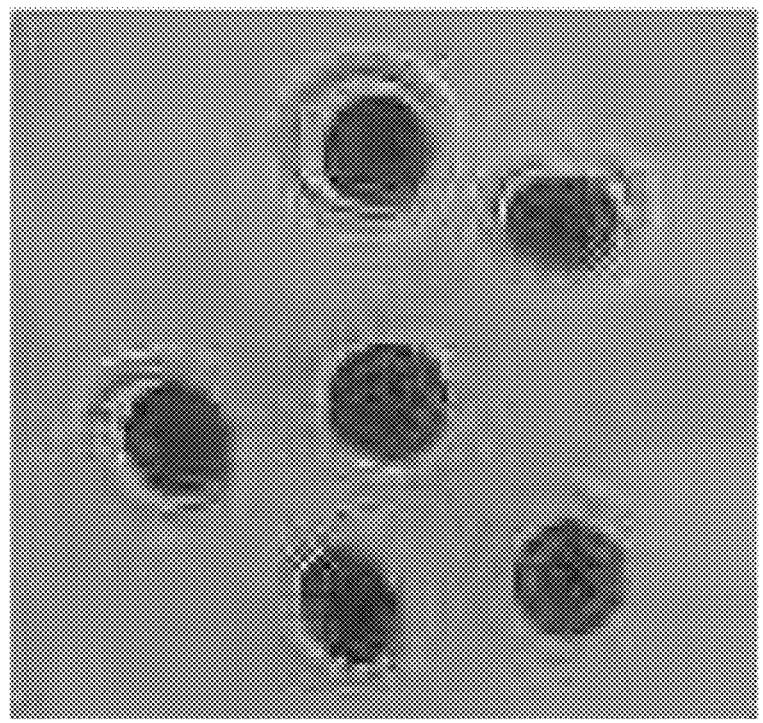
FIG. 4 is a photograph of a state of a mature oocyte in a process of vitrification and thawing of the mature oocyte in a dog.

FIG. 4 shows a photograph of the oocyte treated with the vitrification solution.

The method in accordance with the present disclosure includes a process of placing the oocyte on an oocyte freezing tool and removing the vitrification solution therefrom at a minimum amount and then immediately storing the oocyte in liquid nitrogen (process 2-7).

In the present disclosure, in the process of placing the oocyte on the oocyte freezing tool and removing the vitrification solution therefrom at a minimum amount, the vitrification solution around the oocyte may be removed in an appropriate manner.

An operator may dispose the oocyte on a distal end of the oocyte freezing tool and immerse the tool with the oocyte in the liquid nitrogen and freeze the same. CryoTop (Kitazato, Japan) may be used as the oocyte freezing tool.

As shown in FIG. 1, the CryoTop (Kitazato, Japan) means a tool used to freeze oocytes. The method in accordance with the present disclosure includes a process of thawing the vitrification-frozen oocyte (process 3).

The process of thawing the vitrification-frozen oocyte (process 3) includes: a process of preparing a thawing solution, a dilution solution, a washing solution, and a recovery medium (process 3-1).

Further, the method of thawing the canine oocyte according to the present disclosure may use the thawing solution, dilution solution, washing solution, recovery medium and the above thawing process. Thus, due to the technical characteristics of the thawing solution, dilution solution, washing solution, and recovery medium and thawing process, the viability of the frozen-thawed oocyte is markedly increased, and thus, the frozen-thawed oocyte resulting from the method in accordance with the present disclosure has high nuclear transfer culture effect.

The thawing solution contains sucrose, dextran serum supplement, and HEPES butter solution containing gentamicin sulfate.

In one embodiment, the thawing solution contains 0.5 to 1.5 M of sucrose, 10 to 30% dextran serum supplement, and HEPES butter solution containing 25 to 45 µg/ml of gentamicin sulfate.

In one embodiment, the thawing solution contains 1.0 M of sucrose, 20% dextran serum supplement, and HEPES butter solution containing 35 µg/ml of gentamicin sulfate.

The dilution solution contains sucrose, dextran serum supplement, and HEPES butter solution containing gentamicin sulfate.

In one embodiment, the dilution solution contains 0.3 to 0.7 M of sucrose, 10 to 30% dextran serum supplement, and HEPES butter solution containing 25 to 45 µg/ml of gentamicin sulfate.

In one embodiment, the dilution solution contains 0.5 M of sucrose, 20% dextran serum supplement, and HEPES butter solution containing 35 µg/ml of gentamicin sulfate.

The washing solution contains Dextran Serum Supplement and a HEPES butter solution containing gentamicin sulfate.

In one embodiment, the washing solution contains 15 to 25% Dextran Serum Supplement and a HEPES butter solution containing 25 to 45 μg/ml gentamicin sulfate.

In one embodiment, the washing solution contains 20% Dextran Serum Supplement, and a HEPES butter solution (trade name TCM199) containing 35 μg/ml gentamicin sulfate.

The recovery medium includes a mixture of HEPES butter solution, sodium pyruvate, gentamicin sulfate, FBS (Fetal Bovine Serum).

In one embodiment, the recovery medium includes a mixture of 0.5 to 2 parts by weight of sodium pyruvate, 0.5 to 2 parts by weight of gentamicin sulfate, 2 to 10 parts by weight of Fetal Bovine Serum (FBS), and 100 parts by weight of HEPES butter solution.

The method in accordance with the present disclosure includes a process of heating the thawing solution to 35 to 40° C. in an incubator (process 3-2). In this connection, the thawing solution may be contained in a 25 to 45 mm dish.

In one embodiment, the method in accordance with the present disclosure includes a process of heating 2 to 5 ml of the thawing solution to 37 to 38° C. in an incubator. In this connection, the thawing solution may be contained in a 35 mm dish.

The method in accordance with the present disclosure includes a process of heating the recovery medium to 35 to 40° C. in the incubator (process 3-3).

In one embodiment, the method in accordance with the present disclosure includes a process of heating the recovery medium to 37 to 38° C. in the incubator for 20 to 40 minutes while the recovery medium is dispensed to a 4 well dish.

The method in accordance with the present disclosure includes a process of withdrawing the oocyte freezing tool (CryoTop) stored in the liquid nitrogen and heating the tool and inputting the tool into the thawing solution and then separating the oocyte attached to the oocyte freezing tool (CryoTop) and treating the separated oocyte (process 3-4).

In one embodiment, the method in accordance with the present disclosure includes a process of withdrawing the oocyte freezing tool (CryoTop) stored in the liquid nitrogen and heating the tool and inputting the tool into the thawing solution and then separating the oocyte attached to the oocyte freezing tool (CryoTop) and treating the separated oocyte for 1 minute.

The method in accordance with the present disclosure includes a process of transferring the separated oocyte to a drop of 30 to 50 μl of the dilution solution equilibrated to a room temperature state and treating the oocyte with the dilution solution for 3 to 5 minutes (process 3-5).

In one embodiment, the method in accordance with the present disclosure includes a process of transferring the separated oocyte to a drop of 40 μl of the dilution solution equilibrated to a room temperature state and treating the oocyte with the dilution solution for 4 minutes.

The method in accordance with the present disclosure includes a process of sequentially transferring and treating the treated oocyte to two (each being 30 to 50 μl drop) of the washing solutions equilibrated to a room temperature state for 3 to 5 minutes (process 3-6).

In one embodiment, the method in accordance with the present disclosure includes a process of sequentially transferring and treating the treated oocyte to two (each being 40 μl drop) of the washing solutions equilibrated to a room temperature state for 4 minutes.

The method in accordance with the present disclosure includes a process of transferring the oocyte to the heated recovery medium for recovery culture and then culturing the oocyte in the recovery medium for 1 to 3 hours (process 3-7).

In one embodiment, the method in accordance with the present disclosure includes a process of transferring the oocyte to the heated recovery medium for recovery culture and then culturing the oocyte in the recovery medium for 2 hours.

Figure 5:
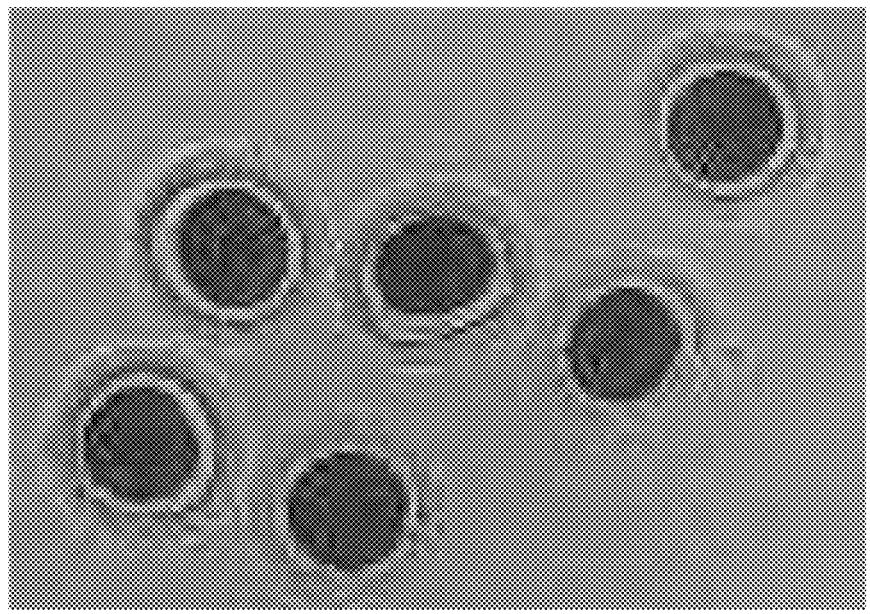
FIG. 5 is a photograph of a state of a mature oocyte in a process of vitrification and thawing of the mature oocyte in a dog.

FIG. 5 is a photograph showing the oocyte treated with the thawing solution.

Figure 6:
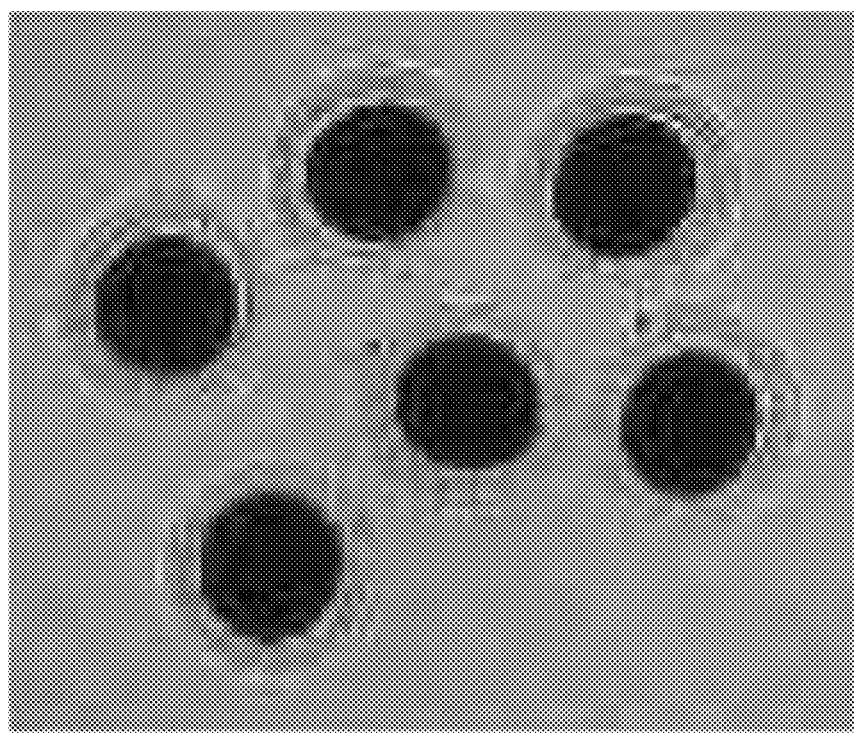
FIG. 6 is a photograph of a state of a mature oocyte in a process of vitrification and thawing of the mature oocyte in a dog.

FIG. 6 is a photograph showing the oocyte treated with the dilution solution.

Figure 7:
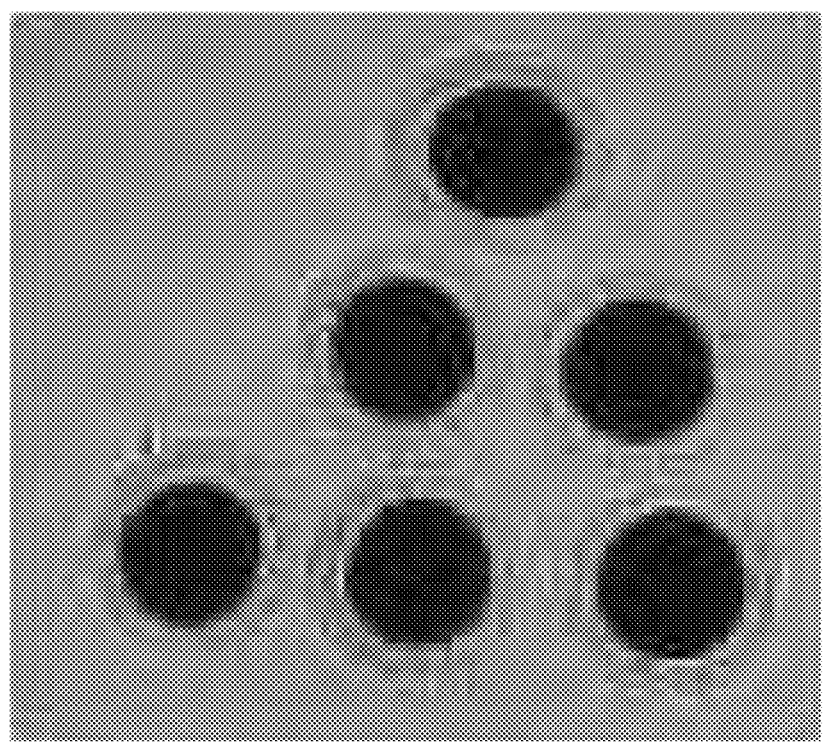
FIG. 7 is a photograph of a state of a mature oocyte in a process of vitrification and thawing of the mature oocyte in a dog.

FIG. 7 is a photograph showing the oocyte treated with the washing solution.

The frozen-thawed oocyte produced by the method for vitrification and thawing of the oocytes of the canine is subjected to the viability test. The results shown in [Table 1] below were obtained.

TABLE 1

| Number of vitrification-frozen oocytes | Viability after thawing of oocyte | Viability after recovery-culturing of oocyte |
| --- | --- | --- |
| 59 | 56(95%) | 53(90%) |

The oocyte viability after thawing the total vitrification-frozen oocytes is very high as 95%. In particular, the oocyte viability after the recovery culture exceeded 90%, showing a significantly higher viability.

Further, efficiency of the present method was examined based on comparison between 90% of mature oocytes (frozen-thawed oocytes) available in the test after the recovery culture and fresh oocytes via a somatic cell nuclear transfer experiment. The efficiency is shown in table 2 below.

TABLE 2

| Control | Culturing | Division (%) | 8 cells (%) | 16 cells (%) | Blastocyst (%) |
| --- | --- | --- | --- | --- | --- |
| Fresh oocyte | 115 | 101(87.8) | 77(67.0) | 51(44.4) | 9(7.8) |
| After thawing | 50 | 29(58.0) | 23(46.0) | 19(38.0) | 3(6.0) |

[Comparison in Efficiency Between Frozen-Thawed Oocytes and Fresh Oocytes]

As shown in the table, no significant defects were found in the frozen-thawed oocytes according to the present disclosure when compared to the fresh oocytes. Similar results were obtained between the frozen-thawed oocytes according to the present disclosure and the fresh oocytes. This suggests that the frozen-thawed oocytes in accordance with the present disclosure have a significantly higher nuclear transfer culture effect.

In other words, we found the similar value in viability between the fresh oocyte and frozen-thawed oocyte according to the present disclosure in blastocyst stage. This may indicate that the frozen-thawed oocytes obtained from the method of the present disclosure have a markedly high nuclear transfer culture effect.

The present disclosure provides the method for vitrification and thawing of canine oocytes and the thus produced frozen-thawed oocytes having the functions and effects as described above.

INDUSTRIAL AVAILABILITY

The method and frozen-thawed oocyte in accordance with the present disclosure are very useful in industries that produce, prepare, sell, distribute and research animal oocytes for somatic cell cloning.

In particular, the method and frozen-thawed oocyte in accordance with the present disclosure are very useful in the production, preparing, sales, distribution, and research of technologies and devices for vitrification and thawing of animal oocytes for somatic cell cloning.

The invention claimed is:

1. A method for vitrification and thawing of an oocyte of a canine, the method comprising:
    a process of collecting a mature oocyte from a canine to form a collected mature oocyte (step 1);
    a process of performing a vitrification of the collected oocyte (step 2),
    wherein the step of performing the vitrification includes steps in the following sequence:
    a step of preparing a mixed liquid, an equilibrium solution, an vitrification solution (step 2-1);
    a step of denuding a cumulus cell of the collected oocyte to form a denuded mature oocyte (step 2-2);
    a step of adding the denuded mature oocyte into the mixed liquid to form a first mixture, wherein the mixed liquid is pre-equilibrated to a room temperature (step 2-3);
    a step of sequential treating the first mixture to form a second mixture in the following order (step 2-4):
    adding the equilibrium solution to the first mixture;
    further adding the mixed liquid to the first mixture,
    further adding the equilibrium solution to the first mixture, and
    further adding the mixed liquid to the first mixture;
    a step of further adding the equilibrium solution to the second mixture to form a third mixture (step 2-5);
    a step of transferring the third mixture into the vitrification solution to form a fourth mixture (step 2-6); and
    a step of placing the fourth mixture on an oocyte freezing tool and removing vitrification solution by a glass pipet therefrom and then immediately storing the occyte freezing tool in liquid nitrogen to form a vitrification-frozen mature oocyte (step 2-7),
    wherein,
    the mixed liquid includes a mixture of 300-1000 parts by weight of modified HTF medium-HEPES with gentamicin (mHTF) and 100 parts by weight of 10 to 30% serum substitute supplement (SSS),
    the equilibrium solution contains 6.5 to 8.5% (v/v) ethylene glycol, 6.5 to 8.5% (v/v) dimethyl sulfoxide, 10 to 30% dextran serum supplement, and a HEPES butter solution containing 25 to 45 µg/ml of gentamicin sulface, and
    the vitrification solution contains 5 to 25% (v/v) ethylene glycol, 5 to 25% (v/v) dimethyl sulfoxide, 10 to 30% dextran serum supplement, 0.3 to 0.6 M of sucrose, and a HEPES butter solution containing 25 to 45 µg/mL gentamicin sulfate.

2. The method of claim 1, wherein the method further comprises a step of thawing the vitrification-frozen oocyte (step 3), after step 2-7,
    wherein the step of thawing the vitrification-frozen oocyte (step 3) includes steps in the following sequence:
    a step of preparing a thawing solution, a dilution solution, two washing solutions, and a recovery medium (step 3-1),
    a step of heating the thawing solution to 35 to 40° C. in an incubator (step 3-2);
    a step of heating the recovery medium to 35 to 40° C. in the incubator (step 3-3);
    a step of withdrawing the oocyte freezing tool from the liquid nitrogen, heating the oocyte freezing tool, inputting the oocyte freezing tool into the thawing solution, separating the mature oocyte from the oocyte freezing tool, and recovering the separated mature oocyte (step 3-4);
    a step of transferring the separated mature oocyte into the dilution solution equilibrated to a room temperature to form a treated mature ooctye (step 3-5);
    a step of sequentially transferring the treated mature oocyte into each of the two washing solutions to form a washed mature oocyte, wherein each of the two washing solutions is pre-equilibrated to a room temperature state (step 3-6); and
    a step of transferring the washed mature oocyte to the heated recovery medium for recovery culture and then culturing the washed mature oocyte in the recovery medium (step 3-7),
    wherein,
    the thawing solution contains 0.5 to 1.5 M of sucrose, 10 to 30% dextran serum supplement, and a HEPES butter solution containing 25 to 45 µg/ml of gentamicin sulfate,
    the dilution solution contains 0.3 to 0.7 M of sucrose, 10 to 30% dextran serum supplement, and a HEPES butter solution containing 25 to 45 µm/ml of gentamicin sulface,
    the washing solution contains 15 to 25% dextran serum supplement and a HEPES butter solution containing 25 to 45 µg/ml gentamicin sulfate, and
    the recovery medium includes a mixture of 0.5 to 2 parts by weight of sodium pyruvate, 0.5 to 2 parts weight of gentamicin sulfate, 2 to 10 parts by weight of fetal bovine serum (FBS), and 100 parts by weight of a HEPES butter solution.

* * * * *